United States Patent
Veigel et al.

(10) Patent No.: US 11,207,137 B2
(45) Date of Patent: Dec. 28, 2021

(54) PATIENT POSITIONING USING A SKELETON MODEL

(71) Applicant: Brainlab AG, Munich (DE)

(72) Inventors: Jochen Veigel, Rosenheim (DE); Ivana Ivanovska, Aschheim (DE); Hagen Kaiser, Icking (DE); Pablo Aponte, Haar (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 16/760,922

(22) PCT Filed: Dec. 7, 2017

(86) PCT No.: PCT/EP2017/081839
§ 371 (c)(1),
(2) Date: May 1, 2020

(87) PCT Pub. No.: WO2019/110105
PCT Pub. Date: Jun. 13, 2019

(65) Prior Publication Data
US 2020/0375661 A1 Dec. 3, 2020

(51) Int. Cl.
*A61B 34/10* (2016.01)
*G06T 15/10* (2011.01)
(Continued)

(52) U.S. Cl.
CPC .............. *A61B 34/10* (2016.02); *G06T 15/10* (2013.01); *G09B 19/003* (2013.01); *A61B 2034/105* (2016.02)

(58) Field of Classification Search
CPC ........ A61B 2034/105; A61B 2090/365; A61B 2090/366; A61B 34/10; A61N 2005/1059;
(Continued)

(56) References Cited

U.S. PATENT DOCUMENTS

| 8,235,530 B2 | 8/2012 | Maad | |
|---|---|---|---|
| 2008/0004517 A1* | 1/2008 | Bhandarkar | G06T 7/33 600/407 |

(Continued)

FOREIGN PATENT DOCUMENTS

| WO | 00/24333 A1 | 5/2000 |
|---|---|---|
| WO | 0024333 A1 | 5/2000 |

(Continued)

OTHER PUBLICATIONS

N. Magnenat-Thalmann, L. Yahia-Cherif and H. Seo, "Modeling Anatomical-Based Humans," Proceedings of the Third International Conference on Image and Graphics (ICIG'04), 2004, IEEE (Year: 2004).*

(Continued)

*Primary Examiner* — Sing-Wai Wu
(74) *Attorney, Agent, or Firm* — Tucker Ellis LLP

(57) ABSTRACT

First and second skeleton model data is determined based on first and second surface data of a patient. Each of the skeleton model data describes geometries of rigid anatomic structures of a patient at a different point in time. Skeleton difference data is determined describing differences between the geometries of the rigid anatomic structures. In a next step, movement instruction data is determined which describes movement to be performed by the rigid anatomic structures to minimize the differences, i.e. to correct the posture of the patient. The movement instruction data is for example determined based on anatomy constraint data which describes anatomical movement constraints for the rigid anatomic structures (e.g. range of motion of a joint). An instruction is displayed (e.g. using augmented reality), guiding the user how to move the rigid anatomic structures so as to correct the patient's posture.

16 Claims, 8 Drawing Sheets

(51) Int. Cl.
*G09B 19/00* (2006.01)
*A61B 90/00* (2016.01)
*A61N 5/10* (2006.01)

(58) Field of Classification Search
CPC .......... A61N 2005/1074; A61N 5/1048; A61N 5/1049; G06T 15/10; G09B 19/003
See application file for complete search history.

(56) References Cited

U.S. PATENT DOCUMENTS

| | | | | |
|---|---|---|---|---|
| 2013/0050225 | A1* | 2/2013 | Nakajima | G06T 13/40 345/473 |
| 2015/0196780 | A1* | 7/2015 | Tijs | A61N 5/1049 600/1 |
| 2019/0366124 | A1* | 12/2019 | Berlinger | A61B 34/10 |

FOREIGN PATENT DOCUMENTS

| | | |
|---|---|---|
| WO | 2012/119649 A1 | 9/2012 |
| WO | 2014/024115 A1 | 2/2014 |
| WO | 2014024115 A1 | 2/2014 |

OTHER PUBLICATIONS

International Search Report and Written Opinion for corresponding International Application No. PCT/EP2017/081839, dated Jul. 5, 2018.
Pollefeys et al., "Metric 3D Surface Reconstruction from Uncalibrated Image Sequences", pp. 139-154, Springer-Verlag Berlin Heidelberg, 1998.
Garcia et al., "Real-Time Human Pose Estimation from Body-Scanned Point Clouds", Mar. 2015.
Zeng et al., "Dense Non-rigid Surface Registration Using High-Order Graph Matching", IEEE Conference on Computer Vision and Pattern Recognition (CVPR), 2010.
Nutti et al., "Depth Sensor-Based Realtime Tumor Tracking for Accurate Radiation Therapy", EUROGRAPHICS, 2014.
Mullaney et al., "PERT Project", Aug. 30, 2017.
Talbot et al., "An Augmented Reality Application for Patient Positioning and Monitoring in Radiotherapy", 2009.
Shotton et al., "Real-Time Human Pose Recognition in Parts from Single Depth Images", Jun. 2011.
Biber et al., "The Normal Distributions Transform: A New Approach to Laser ScanMatching", Nov. 2003.
Besl et al., "A Method for Registration of 3-D Shapes", Feb. 1992.

* cited by examiner

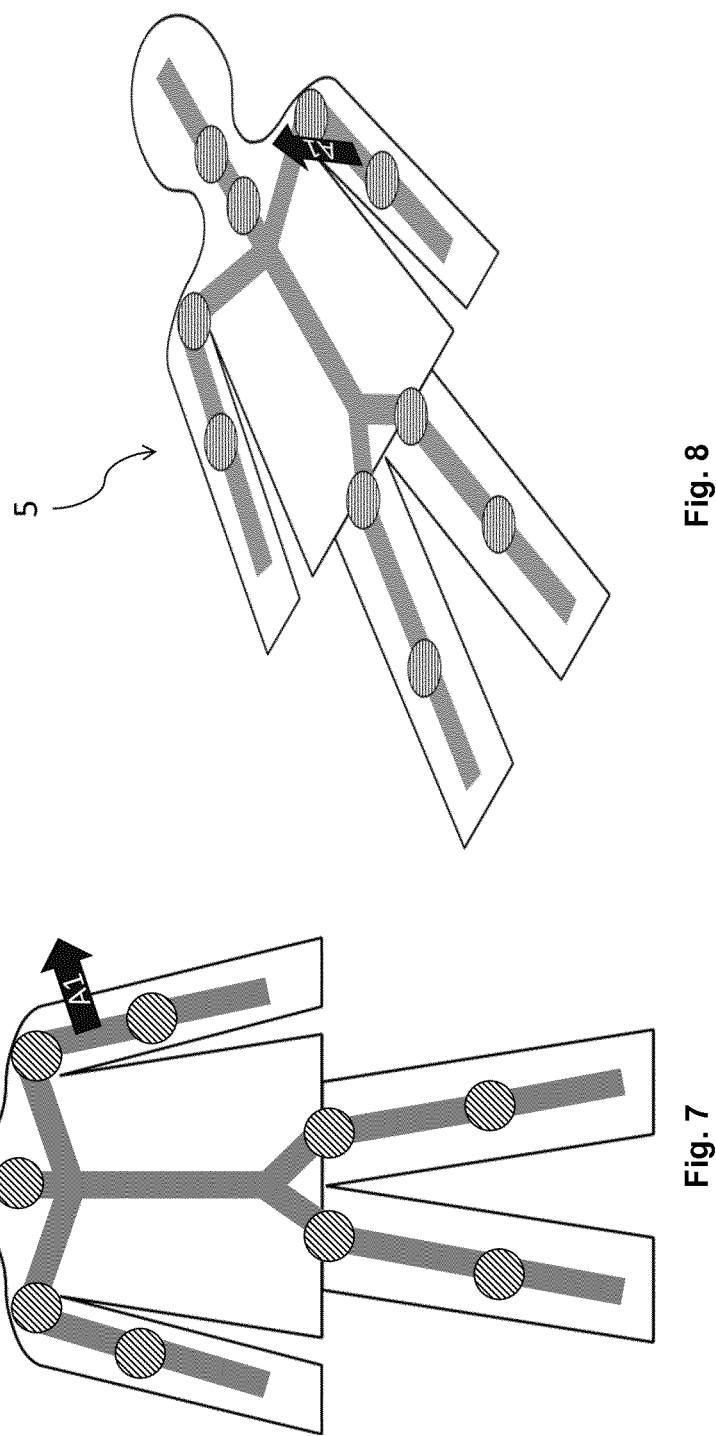

PATIENT POSITIONING USING A SKELETON MODEL

RELATED APPLICATION DATA

This application is a National Phase application of International Application No. PCT/EP2017/081839 filed Dec. 7, 2017, the contents of which are incorporated herein by reference.

FIELD OF THE INVENTION

The present invention relates to a computer-implemented method for determining a movement instruction for correcting the posture of a patient, a corresponding computer program, a non-transitory program storage medium storing such a program and a computer for executing the program, as well as a medical system comprising an electronic data storage device and the aforementioned computer.

TECHNICAL BACKGROUND

In the field of medicine, a patient often needs to be positioned in a certain position and/or posture, such that a target (e.g. a tumor) is in a known relative position to a treatment device (e.g. in the isocenter of a radiotherapy treatment device).

Previous solutions for positioning a patient treated the patient as a rigid object, i.e. they did not take into account any anatomical relationship and limitations (anatomical movement constraints). For example, if the known solutions advise a user to raise the right hand of the patient, the fact that the forearm would most certainly also be raised is not regarded. Furthermore, known solutions are merely capable of displaying discrepancies between positions and/or postures but not capable of displaying instructions of how to correct the patient's posture.

The present invention has the object of determining movement instruction data which describes movement to be performed by rigid anatomic structures of a patient, for correcting the posture of the patient.

The present invention can be used for positioning a patient prior to performing radiotherapy/radiosurgery procedures e.g. in connection with a system for image-guided radiotherapy such as VERO® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses acquiring first surface data describing for example a reference surface and second surface data describing for example a current surface. First skeleton model data is determined based on the first surface data and second skeleton model data is determined based on the second surface data. Each of the skeleton model data describes geometries (e.g. positions and/or orientations) of rigid anatomic structures of the patient such as the upper left arm, the lower left arm, the upper right leg and the lower right leg.

Skeleton difference data is determined describing differences between the geometries (e.g. positions and/or orientations) of the rigid anatomic structures, i.e. describing differences between the first skeleton model data and the second skeleton model data.

In a next step, movement instruction data is determined which describes movement to be performed by the rigid anatomic structures to minimize the differences, i.e. to correct the posture of the patient.

The movement instruction data is for example determined based on (e.g. patient-specific) anatomy constraint data which describes anatomical movement constraints for the rigid anatomic structures (e.g. range of motion of a joint).

An instruction is displayed (e.g. using augmented reality), guiding the user how to move the rigid anatomic structures so as to correct the patient's posture.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method for determining a movement instruction for correcting the posture of a patient. For example, the movement instruction is described by movement instruction data determined by the method. For example, the movement instruction for correcting the posture of a patient is movement to be performed by one or more rigid anatomic structures of the patient in order to minimize a geometrical (e.g. positional) difference to a reference.

The posture of a patient for example specifies the geometries (for example at least one of shapes, positions or orientations) of at least one anatomical body part of the patient. The at least one anatomical body part is for example a limb of the patient such as the lower arm, the upper arm, a hand, a finger, a part of a finger or else. Correcting the posture of the patient for example encompasses moving one or more of the at least one anatomical body parts from a first position to a second position.

The method comprises executing, on at least one processor of at least one computer (for example at least one computer being part of the medical system according to the fifth aspect and/or being the computer according to the fourth aspect), the following exemplary steps which are executed by the at least one processor.

In a (for example first) exemplary step, first surface data is acquired. For example, the first surface data describes a surface of the body of the patient at a first point in time, for example in a first spatial reference system. For example, the first surface data describes a surface of at least a part (e.g. of the body) of the patient at the first point in time. The first surface data for example describes a surface of the patient comprising the surface of the at least a part of the patient (e.g. of the part of the patient) at the first point in time. For example, the at least a part of the patient comprises one or more anatomical body parts of the patient. For example, the first point in time corresponds to a point in time at which a planning image is obtained from the patient (e.g. x-ray image, computer-tomographic (CT) image, cone-beam computer-tomographic (CBCT) image, magnetic resonance (MR) image, ultrasound image or else). The planning image can for example be used to plan a treatment of the patient, for example the irradiation of a certain part of the patient using a treatment beam.

For example, the first surface data is or has been obtained from two-dimensional image data describing at least a part (of the body) of the patient. For example, the first surface data is or has been obtained from two-dimensional image data comprising a series of two-dimensional images. The two-dimensional image data for example comprises at least one of an x-ray image, an ultrasound image, a slice of a three-dimensional image or a photographic image. For example, the two-dimensional image data comprises the (at least one, for example exactly one) planning image(s) obtained at the first point in time. The two-dimensional image data for example comprises a series of images of the same image modality.

For example, the first surface data is obtained from the two-dimensional image data as described by M. Pollefeys et al., "Metric 3D Surface Reconstruction from Uncalibrated Image Sequences", pp. 139-154, Springer-Verlag Berlin Heidelberg, 1998. Applying the method of this example, the first surface data is or has been obtained from two-dimensional image data comprising a sequence of two-dimensional images of the at least one part of the patient. The projective 3D model, the metric 3D (three-dimensional) model or the textured metric 3D surface model described in the above publication are for example described by the first surface data. For example, a metric 3D model is obtained from a series of two-dimensional images of the at least one part of the patient (e.g. as described in the above publication) and described by the first surface data. Other methods of obtaining the first surface data from two-dimensional image data are possible.

For example, the first surface data is or has been obtained from three-dimensional image data describing at least a part (of the body) of the patient. For example, the first surface data is or has been obtained from three-dimensional image data describing the body of the patient. For example, the three-dimensional image data comprises at least one of a cone-beam (CB) computer-tomographic (CT) image, a magnetic resonance (MR) image and a depth-image (e.g. a parallax image). For example, the three-dimensional image data comprises the (at least one, for example exactly one) planning image(s) obtained at the first point in time. The three-dimensional image data may be generated based on an anatomical atlas and an image of at least a part of the patient. The three-dimensional image data may be generated (determined) using one or more surface cameras (e.g. infrared, time-of-flight, stereoscopic, 3D scanner, LIDAR, range camera, laser scanner, or else) which capture the at least a part of the patient. For example, the first surface data is or has been obtained from the projective 3D (three-dimensional) model, the metric 3D model or the textured metric 3D surface model described above. For example, an outer contour of the at least a part of the patient is determined as the surface of the at least a part of the patient. A suitable method to determine an outer contour of the at least a part of the patient may be used, for example a gradient-based method for CT (computer-tomographic) image data. The surface of the at least a part of the patient is for example indicated in the three-dimensional image data, for example in case the three-dimensional image data was generated based on an anatomical atlas.

In a (for example second) exemplary step, first skeleton model data is determined. For example, the first skeleton model data is determined based on the first surface data (e.g. from the first surface data). For example, the first skeleton model data describes first geometries (for example at least one of shapes, positions or orientations) of one or more rigid anatomic structures, for example in the first spatial reference system. The geometries constitute a single set of at least one of shapes, positions or orientations of the one or more rigid anatomic structures. For example, for each of the one or more rigid anatomic structures, the set comprises one (for example, exactly or only one) shape and/or position (for example, position relative to another one of the rigid anatomic structures) and/or orientation. For example, the one or more rigid anatomic structures are one or more anatomical body parts of the patient. For example, the first skeleton model data is determined as described in J. Shotton, et al.: "Real-time human pose recognition in parts from single depth images", IEEE Conference on Computer Vision and Pattern Recognition (CVPR), 2011, pp. 1297-1304 based on the first surface data. For example, the first skeleton model data is determined as described by Garcia et al.: "Real-Time Human Pose Estimation from Body-Scanned Point Clouds", International Conference on Computer Vision Theory and Applications, March 2015, Berlin, Germany, wherein the body-scanned point clouds correspond to the first surface data and the pose estimation corresponds to the first geometries described by the first skeleton mode data. Alternatively and/or additionally, SDK tools for Microsoft's Kinect® can be used to determine the first skeleton model data based on the first surface data.

For example, each of the one or more rigid anatomic structures is an anatomic body part which can be moved individually and/or intentionally by the patient. For example, each of the one or more rigid anatomic structures is an anatomic body part which can be moved by the patient at will. The one or more rigid anatomic structures (and/or the one or more anatomical body parts) are for example a limb of the patient such as the lower arm, the upper arm, a hand, a finger, a part of a finger or else. For example, the one or more rigid anatomic structures are anatomic structures of the patient which each cannot be deformed (e.g. compressed, extended, bent) more than a predetermined threshold. This threshold is for example 0.01 mm, 0.1 mm, 1 mm or more. For example, the one or more rigid anatomic structures are anatomic structures of the patient which each cannot be deformed in a given spatial direction more than a predetermined threshold for the spatial direction. For example, the one or more rigid anatomic structures are anatomic structures of the patient which each comprise a different bone. For example, the one or more rigid anatomic structures are anatomic structures of the patient which geometry is defined by a single bone (e.g. femur, humerus or else) or by a plurality of bones (e.g. a plurality of vertebrae, a plurality of ribs or else) which cannot move more than a predetermined amount in relation to one another. For example, each of the one or more rigid anatomic structures of the patient has an individual first geometry (for example at least one of a shape, position or orientation).

In a (for example third) exemplary step, second surface data is acquired. The second surface data for example describes a surface of the patient at a second point in time, for example in a second spatial reference system. For example, a transformation between the first and the second spatial reference system is predetermined (i.e. at least one of fixed or known). For example, the second surface data describes a surface of the body of the patient at a second point in time. For example, the second surface data describes a surface of at least a part (e.g. of the body) of the patient at the second point in time. For example, the second surface data describes a surface of the patient at the second point in time. The second surface data for example describes a surface of the patient comprising the surface of the at least a part of the patient (e.g. of the part of the patient) at the second point in time. For example, the at least a part of the patient comprises one or more anatomical body parts of the patient. For example, the second point in time corresponds to a point in time at which a registration image is obtained from the patient (e.g. x-ray image, computer-tomographic (CT) image, cone-beam computer-tomographic (CBCT) image, magnetic resonance (MR) image, ultrasound image or else). The registration image can for example be used to register a planning image to the current pose and posture of the patient.

For example, the second surface data is or has been obtained from two-dimensional image data describing at least a part (of the body) of the patient, for example the same part of the patient described by the first surface data. For example, the second surface data is or has been obtained from two-dimensional image data comprising a series of two-dimensional images. The two-dimensional image data for example comprises at least one of an x-ray image, an ultrasound image, a slice of a three-dimensional image or a photographic image. For example, the two-dimensional image data comprises the (at least one, for example exactly one) image(s) obtained at the second point in time. The two-dimensional image data for example comprises a series of images of the same image modality.

For example, the second surface data is obtained from the two-dimensional image data as described by M. Pollefeys et al., "Metric 3D Surface Reconstruction from Uncalibrated Image Sequences", pp. 139-154, Springer-Verlag Berlin Heidelberg, 1998. Applying the method of this example, the second surface data is or has been obtained from two-dimensional image data comprising a sequence of two-dimensional images of the at least one part of the patient, for example the same part of the patient described by the first surface data. The projective 3D model, the metric 3D (three-dimensional) model or the textured metric 3D surface model described in the above publication are for example described by the second surface data. For example, a metric 3D model is obtained from a series of two-dimensional images of the at least one part of the patient (e.g. as described in the above publication) and described by the second surface data. Other methods of obtaining the second surface data from two-dimensional image data are possible.

For example, the second surface data is or has been obtained from three-dimensional image data describing at least a part (of the body) of the patient, for example the same part of the patient described by the first surface data. For example, the second surface data is or has been obtained from three-dimensional image data describing the body of the patient. For example, the three-dimensional image data comprises at least one of a cone-beam (CB) computer-tomographic (CT) image, a magnetic resonance (MR) image and a depth-image (e.g. a parallax image). For example, the three-dimensional image data comprises the (at least one, for example exactly one) image(s) obtained at the second point in time. The three-dimensional image data may be generated based on an anatomical atlas and an image of at least a part of the patient. The three-dimensional image data may be generated (determined) using one or more surface cameras (e.g. infrared, time-of-flight, stereoscopic, 3D scanner, LIDAR, range camera, laser scanner or else) which capture the at least a part of the patient. For example, the second surface data is or has been obtained from the projective 3D (three-dimensional) model, the metric 3D model or the textured metric 3D surface model described above. For example, an outer contour of the at least a part of the patient is determined as the surface of the at least a part of the patient. A suitable method to determine an outer contour of the at least a part of the patient may be used, for example a gradient-based method for CT (computer-tomographic) image data. The surface of the at least a part of the patient is for example indicated in the three-dimensional image data, for example in case the three-dimensional image data was generated based on an anatomical atlas.

In a (for example fourth) exemplary step, second skeleton model data is determined. For example, the second skeleton model data is determined based on the second surface data (e.g. from the second surface data). For example, the second skeleton model data describes second geometries (for example at least one of shapes, positions or orientations) of one or more rigid anatomic structures, for example in the second spatial reference system. The geometries constitute a single set of at least one of shapes, positions or orientations of the one or more rigid anatomic structures. For example, for each of the one or more rigid anatomic structures, the set comprises one (for example, exactly or only one) shape and/or position (for example, position relative to another one of the rigid anatomic structures) and/or orientation. For example, the one or more rigid anatomic structures are one or more anatomical body parts of the patient. For example, the second skeleton model data describes second geometries (for example at least one of shapes, positions or orientations) of the one or more rigid anatomic structures, of which the first skeleton model data describes the first geometries. For example, the second skeleton model data is determined as described in J. Shotton, et al.: "Real-time human pose recognition in parts from single depth images", IEEE Conference on Computer Vision and Pattern Recognition (CVPR), 2011, pp. 1297-1304, based on the second surface data. For example, the second skeleton model data is determined as described by Garcia et al.: "Real-Time Human Pose Estimation from Body-Scanned Point Clouds", International Conference on Computer Vision Theory and Applications, March 2015, Berlin, Germany, wherein the body-scanned point clouds correspond to the second surface data and the pose estimation corresponds to the second geometries described by the second skeleton mode data. Alternatively and/or additionally, a SDK (software development kit) for Microsoft's Kinect® camera device can be used to determine the second skeleton model data based on the second surface data.

In a (for example fifth) exemplary step, skeleton difference data is determined. For example, the skeleton difference data is determined based on the first skeleton model data and the second skeleton model data. For example, the skeleton difference data is determined furthermore based on the transformation between the first and the second spatial reference system. For example, the skeleton difference data describes a difference (e.g. translation and/or rotation) between the first geometries (for example at least one of shapes, positions or orientations of rigid anatomical body parts described by the first skeleton model data) and the second geometries (for example at least one of shapes, positions or orientations of rigid anatomical body parts described by the second skeleton model data). For example, the skeleton difference data describes a difference between the first geometry of a first anatomical body part and the second geometry of the first anatomical body part. For example, the skeleton difference data describes a difference between the first geometry of a second anatomical body part and the second geometry of the second anatomical body part. For example, the skeleton difference data describes a difference between the first geometry of each of the one or more rigid anatomic structures and the second geometry of each of the one or more rigid anatomic structures. For example, the skeleton difference data describes the difference for each of at least a subset (for example, strict subset) of the one or more rigid anatomic structures. For example, the skeleton difference data describes an individual difference for each (or for the subset) of the one or more rigid anatomic structures.

For example, the skeleton difference data comprises a transformation matrix. For example, the transformation matrix specifies a linear transformation between a third spatial reference system (e.g. describing the first geometry of a first rigid anatomic structure) and a fourth spatial reference system (e.g. describing the second geometry of the first rigid anatomic structure), for example comprising translational and/or rotatory components and/or scaling factors. For example, the transformation matrix specifies a linear transformation between a first geometry in the first spatial reference system and a second geometry in the second spatial reference system, for example of a corresponding (e.g. of the same) rigid anatomic structure. For example, the transformation matrix specifies a transformation for one of the anatomic rigid structures described by the first skeleton model data to a corresponding anatomic rigid structure described by the second skeleton model data, i.e. specifies a transformation of the first geometry into the second geometry or vice versa. For example, the skeleton difference data comprises a transformation matrix between at least one (for example between all) of the first and second geometries described by the first and second skeleton model data.

For example, it is determined which of the first geometries corresponds to which of the second geometries. For example, it is determined that the first geometry of a first rigid anatomic structure corresponds to a second geometry of the first rigid anatomic structure and so on. In other words, it is for example determined that a first geometry corresponds to a second geometry in case the first geometry is a geometry of a specific rigid anatomic structure and the second geometry is a geometry of the same specific rigid anatomic structure. It is for example determined which of the first geometries corresponds to which of the second geometries based on atlas data. For example, the first surface data is matched with atlas data. For example, an atlas image is fused (see chapter "Definitions") with an image of the first surface data. After this image fusion, it can for example be determined which of the anatomical body parts described by the atlas data corresponds to which of the rigid anatomic structures described by the first surface data. For example, the second surface data is matched with atlas data. For example, an atlas image is fused (see chapter "Definitions") with an image of the second surface data. After this image fusion, it can for example be determined which of the anatomical body parts described by the atlas data corresponds to which of the rigid anatomic structures described by the second surface data. For example, it can then be determined which of the rigid anatomic structures described by the first surface data corresponds to which of the rigid anatomic structures described by the second surface data (i.e. which of the first geometries corresponds to which of the second geometries), based on the determination of the corresponding anatomical body parts. For example, it is determined that (e.g. a first geometry of) a first rigid anatomic structure described by the first surface data, which is or has been determined to correspond to a first anatomical body part, corresponds to (e.g. a second geometry of) a first rigid anatomic structure described by the second surface data, which is or has been determined to correspond to the first anatomical body part.

In a (for example sixth) exemplary step, movement instruction data is determined. For example, the movement instruction data is determined based on the skeleton difference data and the second skeleton model data. For example, the movement instruction data describes movement to be performed by the one or more rigid anatomic structures in order to minimize the difference (described by the skeleton difference data).

Movement instruction data is for example determined and/or stored in the form of a list of vectors, and/or rotation and/or translation matrices. For example, the list is ordered to indicate the order in which the movement instructions are displayed. For example, the list is ordered to indicate the order of the determination of the movement to be performed by the one or more rigid anatomic structures.

The movement instruction data is for example determined starting with the determination of the movement to be performed by one or more rigid anatomic structures comprised in the same limb of the patient. For example, the movement instruction data is determined starting with the determination of the movement to be performed by those of the one or more rigid anatomic structures which are comprised in the same limb of the patient. For example, the one or more rigid anatomic structures for which the movement instruction data is determined are the one or more rigid anatomic structures which geometries are described by the first and/or second skeleton model data. For example, the one or more rigid anatomic structures for which the movement instruction data is determined are a subset (a selection) of the one or more rigid anatomic structures which geometries are described by the first and/or second skeleton model data.

For example, the movement instruction data is determined for all rigid anatomic structures comprised in the same limb of the patient. For example a limb according to this application is the left arm, the right arm, the left leg, the right leg, the head, the neck, the head including the neck, the torso, the left arm including the left hand, the right arm including the right hand, the left leg including the left foot or the right leg including the right foot. For example, the movement instruction data is determined starting with the determination of movement to be performed by a first rigid anatomic structure comprised in a first limb of a patient. For example, the movement instruction data is then determined continuing with the determination of movement to be performed by a second rigid anatomic structure comprised in the first limb of the patient. For example, the first and second rigid anatomic structures are in contact with each other and/or are neighboring rigid anatomic structures and/or are linked via (one or more, for example exactly one) anatomical joint(s). For example, the first rigid anatomic structure is linked via an anatomical joint with the second rigid anatomic structure, both the first and the second rigid anatomic structure being comprised in the same limb of the patient. For example, the first rigid anatomic structure is the upper left arm of the patient and the second rigid anatomic structure is the lower left arm of the patient, the first rigid anatomic structure and the second rigid anatomic structure being linked via the left cubital joint (the left elbow joint).

After determining the movement to be performed by the rigid anatomic structures in the first limb, the method for example proceeds with determining the movement to be performed by one or more rigid anatomic structures comprised in a second limb of the patient which is different from the first limb. For example, after determining the movement to be performed by the rigid anatomic structures of the first limb of the patient, the method proceeds with determining the movement to be performed by a third rigid anatomic structure comprised in a second limb of a patient. For example, the method then proceeds with the determination of the movement to be performed by a fourth rigid anatomic structure comprised in the second limb of the patient. For example, the third rigid anatomic structure is linked via an anatomical joint with the fourth rigid anatomic structure, both the third and the fourth rigid anatomic structure being comprised in the same limb of the patient. For example, the third rigid anatomic structure is the lower right arm of the patient and the fourth rigid anatomic structure is the right hand of the patient, the third rigid anatomic structure and the fourth rigid anatomic structure being linked via the right carpus (the right wrist).

For example, it is determined which of the one or more rigid anatomic structures are comprised in the same limb based on the first and/or second skeleton model data and/or based on atlas data (e.g. matched to the first and/or second surface data).

The movement instruction data is for example determined starting with the determination of the movement to be performed by the most proximal of the one or more rigid anatomic structures and/or ending with the determination of the movement to be performed by the most distal of the one or more rigid anatomic structures.

For example, the movement instruction data is determined starting with the determination of the movement to be performed by the most proximal of the one or more rigid anatomic structures and continues with the determination of the movement to be performed by the second-most proximal of the one or more rigid anatomic structures. For example, the movement instruction data is determined ending with the determination of the movement to be performed by the most distal of the one or more rigid anatomic structures after determining the movement to be performed by the second-most distal of the one or more rigid anatomic structures.

For example, the movement instruction data is determined starting with the determination of the movement to be performed by the most proximal of the rigid anatomic structures comprised in a first limb of a patient. For example, the method proceeds with the determination of the movement to be performed by the second-most proximal of the rigid anatomic structures comprised in the same (the first) limb of the patient. For example, after determining the movement to be performed for all rigid anatomic body parts comprised in the same (the first) limb of the patient, the method proceeds with the determination of the movement to be performed by the most proximal of the rigid anatomic structures comprised in a second limb of the patient. For example, the method proceeds with the determination of the movement to be performed by the second-most proximal of the rigid anatomic structures comprised in the same (the second) limb of the patient.

For example, it is determined which of the one or more rigid anatomic structures is more anatomically distal and which is more anatomically proximal, based on the first and/or second skeleton model data and/or based on atlas data (e.g. matched to the first and/or second surface data as described above).

In a further exemplary step of the method according to the first aspect, anatomy constraint data is acquired. For example, the anatomy constraint data describes anatomical movement constraints for the one or more rigid anatomic structures. For example, the anatomy constraint data describes range of motion for the one or more rigid anatomic structures. For example, the anatomy constraint data describes a range of motion for the one or more rigid anatomic structures in relation to a neighboring/adjacent rigid anatomic structure. For example, the anatomy constraint data describes a range of motion for a link (e.g. an anatomical joint or a virtual joint) between two of the one or more rigid anatomic structures. For example, the anatomy constraint data describes a range of motion for all links of the one or more rigid anatomic structures. For example, the range of motion is defined with respect to the neutral bone position (see chapter "Definitions" below) between two of the one or more rigid anatomic structures. For example, the anatomy constraint data is determined based on predetermined values (e.g. angles, ranges of angles, amounts of distance (for example into a given spatial direction) or else) describing degrees and amounts of freedom (e.g. translational and/or rotatory) for the respective links between the rigid anatomic structures (e.g. based on predetermined ranges of motion of anatomical joints of a human or based on predetermined ranges of motion of virtual joints between two rigid anatomic body parts (e.g. a virtual joint between the spine and the upper left leg, a virtual joint between a first portion of the spine and a second portion of the spine or else)).

For example, the anatomy constraint data is obtained based on, e.g. from, atlas data. For example, atlas data is matched to the first and/or second surface data as described above. The one or more rigid anatomic structures described by the first and/or second skeleton model data are for example anatomically identified (correct anatomical functions assigned, e.g. identified as upper left arm or lower right arm) based on the atlas data after the matching, i.e. the anatomical body parts described by the atlas data corresponding to the rigid structures are identified. For example, after matching the atlas data with the first and/or second skeleton model, the anatomical movement constraints of the identified rigid anatomic structures can be obtained from the atlas, thereby determining the anatomy constraint data. For example, the anatomical movement constraints of the anatomical body parts described by the atlas data which correspond to the rigid structures are obtained as the anatomical movement constraints of the rigid structures. For example, the anatomical movement constraints of the anatomical body parts are described by the atlas data, for example (non-)patient specific and/or (non-)indication-specific atlas data.

For example, the movement instruction data is determined (furthermore) based on the anatomy constraint data. For example, the movement instruction data is determined taking into account the anatomical movement constraints of each of the one or more rigid anatomic structures. For example, the determined movement instruction data does not describe movements to be performed by rigid anatomic structures which would contradict the anatomical movement constraints described by the anatomy constraint data. For example, the skeleton difference data describes a first difference between a first geometry and a second geometry of a first rigid anatomic structure (e.g. the lower left arm). In this example, the movement instruction data is determined based on the anatomical movement constraints of the link (e.g. the left elbow joint) between the first rigid anatomic structure (e.g. the lower left arm) and a second rigid anatomic structure (e.g. the upper left arm). This for example prevents movement of the rigid anatomic structure by a user which injures and/or hurts the patient. For example, the anatomic movement constraint in this case specifies a range of motion of the link (e.g. the left elbow joint) between the first rigid anatomic structure (e.g. the lower left arm) and a second rigid anatomic structure (e.g. the upper left arm). For example, the determined movement instruction data does not describe movements to be performed by rigid anatomic structures which contradict (i.e. are outside of) the range of motion of this link. For example, in case the movement to be performed by the first rigid anatomic structure exceeds an anatomical movement constraint (e.g. more than a predetermined threshold), the movement instruction data is determined such that it describes not only the movement to be performed by the first rigid anatomic structure (e.g. the lower left arm) but also the movement to be performed by the second rigid anatomic structure (e.g. the upper left arm). This determination is for example performed for a plurality of the one or more rigid anatomic structures, for example for all rigid anatomic structures. For example, this determination is performed such that the movement instruction data describes the movements to be performed by the smallest possible number of rigid anatomic structures so that the difference described by the skeleton difference data is minimized (e.g. minimized to zero or below a predetermined threshold), for example whilst taking into account the anatomical movement constraints using the anatomy constraint data for the determination.

For example, the anatomy constraint data describes the anatomical movement constraints for at least one of the one or more rigid anatomic structures specifically for the patient and/or specifically for a (medical) indication. For example, the anatomy constraint data is determined using predetermined values for the respective links (e.g. anatomical joints) between the rigid anatomic structures (e.g. bones) of the patient (e.g. based on predetermined ranges of motion of anatomical joints of the patient).

In a further exemplary step of the method according to the first aspect, surface deviation data is determined. For example, the surface deviation data is determined based on the first surface data and the second surface data. For example, the surface deviation data describes deviations between the surface of the body of the patient at the first point in time and the surface of the body of the patient at the second point in time. For example, the surface deviation data describes a difference in the geometry (for example at least one of shape, position or orientation) of the surface of the body of the patient at the first point in time and the geometry (for example at least one of shape, position or orientation) of the surface of the body of the patient at the second point in time. For example, the surface deviation data describes a positional difference between the surface of the body of the patient at the first point in time and the surface of the body of the patient at the second point in time. For example, the surface deviation data describes a transformation (for example in the form of one or more transformation matrices, one more deformation vectors, a deformation field) between the surface of the body of the patient at the first point in time and the surface of the body of the patient at the second point in time (e.g. comprising translational and/or rotatory shifts). For example, a suitable surface-to-surface matching algorithm can be used to determine the surface deviation data (i.e. a 3D-surface-to-3D-surface matching algorithm). For example, the algorithmic framework for non-rigid surface matching as described by Zeng et al., "Dense Non-rigid Surface Registration Using High-Order Graph Matching", IEEE Conference on Computer Vision and Pattern Recognition (CVPR), 2010, is used to determine the surface deviation data.

In a further exemplary step of the method according to the first aspect, target data is acquired. The target data for example describes a geometry (i.e. at least one of shape, position or orientation) of a target for treatment (e.g. a tumor) at the first point in time. For example, the target data describes the geometry of a target for treatment in a fifth spatial reference system. For example, the fifth spatial reference system is equal to the first spatial reference system and/or the second spatial reference system. For example, the target data includes transformation data describing a transformation between the fifth spatial reference system and at least one of the first and the second spatial reference system. For example, the first spatial reference system is equal to the second spatial reference system. For example, the spatial reference system in which the surface of the patient is described by the first surface data is equal to the spatial reference system in which the surface of the patient is described by the second surface data.

In a further exemplary step of the method according to the first aspect, corrected target data is determined. The corrected target data is for example determined based on the surface deviation data and based on the target data. For example, the corrected target data is determined based on the surface deviation data and based on the target data as described by Nutti et al.: "Depth Sensor-Based Realtime Tumor Tracking for Accurate Radiation Therapy", EUROGRAPHICS, 2014. In this example, a volumetric (e.g. finite element model (FEM-)) model of the patient is deformed based on the surface deviation data. This for example results in another geometry of the target which lies in the volumetric model of the patient, which another geometry is for example described by the corrected target data. For example, the corrected target data describes the geometry of the target at the second point in time.

In a further exemplary step of the method according to the first aspect, movement instruction display data is determined. For example, movement instruction display data is determined based on the movement instruction data. For example, the movement instruction display data describes an instruction specifying movement to be performed by at least one rigid anatomic structure. For example, the movement instruction display data describes an instruction in the form of an arrow, a color code, a number or else, for example for one or more of the one or more rigid anatomic structures.

In a further exemplary step of the method according to the first aspect, a display device (e.g. a display screen, an augmented reality device and/or a light projecting device) is controlled. For example, the display device is controlled to output the instruction. For example, the display device is controlled to output the instruction based on the movement instruction display data. For example, the instruction is projected onto a plane, for example onto the surface of the body of the patient. For example, the instruction is displayed in an augmented reality device (e.g. augmented reality glasses) together with an image of the patient. For example, the instruction has the form of color-coding, numbers, arrows, lines, contours, symbols, text, vectors, curved arrows, animations, the desired pose/posture of the patient or combinations thereof. For example, the desired posed is displayed using an opaque or partially transparent representation of a human body, for example the patient. For example, the representation of the human body is a simplification of the actual human body (of the patient).

For example, the instruction specifies movement to be performed by those of the one or more rigid anatomic structures which are comprised in the same limb of the patient. For example, the instruction specifies movement to be performed by a first rigid anatomic structure comprised in a first limb and movement to be performed by a second rigid anatomic structure comprised in the first limb, for example subsequently. For example, the instruction specifies movement to be performed by one rigid anatomic structure in a first limb and after this rigid anatomic structure is/has been moved more than a predetermined threshold (for example 1 mm, 5 mm, 10 mm, 15 mm or more), specifies movement to be performed by another rigid anatomic structure in the first limb. For example, this has the advantage that a user and/or the patient is instructed to move one limb of the patient after another, thereby avoiding mistakes and saving time for adjusting the patient's pose.

For example, the instruction specifies movement to be performed by the most proximal of the one or more rigid anatomic structures. For example, the instruction specifies movement to be performed by a first rigid anatomic structure and movement to be performed by a second rigid anatomic structure which is more distal than the first rigid anatomic structure, for example subsequently. For example, the instruction specifies movement to be performed by one proximal rigid anatomic structure and after this rigid anatomic structure is or has been moved more than a predetermined threshold, specifies movement to be performed by another rigid anatomic structure which is more distal. These anatomic structures may also be comprised in the same limb as noted above. In this case the instruction specifies movement to be performed for rigid anatomic body parts in the following order: The most proximal of a first limb, the second-most proximal in the first limb, ( . . . ) the most distal in the first limb, the most proximal in a second limb, the second-most proximal in the second limb, ( . . . ) the most distal in the second limb and so on. For example, this has the advantage that a user and/or the patient is instructed to move the most proximal rigid anatomic body part before moving the more distal rigid anatomic body parts, thereby avoiding injury of the patient, avoiding mistakes and saving time for adjusting the patient's pose. For example, the instruction is interpreted by a patient positioning robot which moves the patient in accordance with the instruction.

In a further exemplary step of the method according to the first aspect, target display data is determined. For example, the target display data is determined based on the corrected target data. For example, the target display data describes a virtual object corresponding to the geometry (for example at least one of shape, position or orientation) of the target at the second point in time.

In a further exemplary step of the method according to the first aspect, a display device is controlled (e.g. the aforementioned display device). For example, the display device is controlled based on the target display data. For example, the display device is controlled based on the target display data to output the virtual object.

In a further exemplary step of the method according to the first aspect, third surface data is acquired. The third surface data is for example two-dimensional image data or three-dimensional image data.

For example, the third surface data is or has been obtained from two-dimensional image data describing at least a part (of the body) of the patient, for example the same part of the patient described by the first and/or second surface data. For example, the third surface data is or has been obtained from two-dimensional image data comprising a series of two-dimensional images. The two-dimensional image data for example comprises at least one of an x-ray image, an ultrasound image, a slice of a three-dimensional image or a photographic image. For example, the two-dimensional image data comprises the (at least one, for example exactly one) image(s) obtained at the second point in time. The two-dimensional image data for example comprises a series of images of the same image modality.

For example, the third surface data is obtained from the two-dimensional image data as described by M. Pollefeys et al., "Metric 3D Surface Reconstruction from Uncalibrated Image Sequences", pp. 139-154, Springer-Verlag Berlin Heidelberg, 1998. Applying the method of this example, the third surface data is or has been obtained from two-dimensional image data comprising a sequence of two-dimensional images of the at least one part of the patient, for example the same part of the patient described by the first and/or second surface data. The projective 3D model, the metric 3D (three-dimensional) model or the textured metric 3D surface model described in the above publication are for example described by the third surface data. For example, a metric 3D model is obtained from a series of two-dimensional images of the at least one part of the patient (e.g. as described in the above publication) and described by the third surface data. Other methods of obtaining the third surface data from two-dimensional image data are possible.

For example, the third surface data is or has been obtained from three-dimensional image data describing at least a part (of the body) of the patient, for example the same part of the patient described by the first and/or second surface data. For example, the third surface data is or has been obtained from three-dimensional image data describing the body of the patient. For example, the three-dimensional image data comprises at least one of a cone-beam (CB) computer-tomographic (CT) image, a magnetic resonance (MR) image and a depth-image (e.g. a parallax image). For example, the three-dimensional image data comprises the (at least one, for example exactly one) image(s) obtained at the second point in time. The three-dimensional image data may be generated based on an anatomical atlas and an image of at least a part of the patient. The three-dimensional image data may be generated (determined) using one or more surface cameras (e.g. infrared, time-of-flight, stereoscopic, 3D scanner, LIDAR, range camera, laser scanner or else) which capture the at least a part of the patient. For example, the third surface data is or has been obtained from the projective 3D (three-dimensional) model, the metric 3D model or the textured metric 3D surface model described above. For example, an outer contour of the at least a part of the patient is determined as the surface of the at least a part of the patient. A suitable method to determine an outer contour of the at least a part of the patient may be used, for example a gradient-based method for CT (computer-tomographic) image data. The surface of the at least a part of the patient is for example indicated in the three-dimensional image data, for example in case the three-dimensional image data was generated based on an anatomical atlas.

For example, the third surface data describes a surface of the body of the patient at a third point in time. For example, the third surface data describes at least a surface of at least one rigid anatomic structure of the patient at the third point in time. For example, the third surface data describes at least a surface of at least one rigid anatomic structure of the patient at the third point in time, wherein the at least one rigid anatomic structure of the patient is or has been moved compared with the second point in time, for example based on the instruction.

In a further exemplary step of the method according to the first aspect, decision data (e.g. binary decision data) is determined. For example, the decision data is determined based on the second surface data and the third surface data. For example, the decision data specifies whether the geometry (for example at least one of shape, position or orientation) of a rigid anatomic structure of the patient has changed (whether the posture of the patient has changed) between the second point in time and the third point in time.

In a further exemplary step of the method according to the first aspect, the method is repeated starting with the step of acquiring the second patient surface data. For example, the method is repeated if the decision data specifies that the posture of the patient has changed between the second point in time and the third point in time. For example, during repeating the method, the third point in time is used as the second point in time (i.e. a loop is performed, subsequently updating the second surface data and the second skeleton model data). For example, the repeating of the method is stopped in case the skeleton difference data fulfills predetermined criteria, e.g. one or more threshold values. For example, the threshold value is 0.1 mm, 1 mm, 2 mm, 5 mm, 10 mm, 20 mm, 2 cm, 5 cm, for example between 1 cm and 2 cm.

For example, the first point in time is earlier than the second point in time. For example, the second point in time is earlier than the third point in time. For example, while repeating the method, the third point in time is used as the second point in time.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
  a. the at least one computer (2) according to the fourth aspect;
  b. at least one electronic data storage device (3) storing at least the first surface data; and
  c. a medical device (4) (e.g. including a surface camera, a patient couch, a treatment device for radiotherapy/radiosurgery or else) for carrying out a medical procedure on the patient, the medical device comprising a display device (e.g. monitor display, augmented reality device, light projecting device or else),
  wherein the at least one computer is operably coupled to
    the at least one electronic data storage device for acquiring, from the at least one data storage device, at least the first surface data, and
    the medical device for issuing a control signal to the medical device for controlling, on the basis of the movement instruction data,
      displaying, by the display device, an instruction specifying movement to be performed by one or more rigid anatomic structures of the patient.

For example, the invention does not involve or in particular comprise or encompass an invasive step which would represent a substantial physical interference with the body requiring professional medical expertise to be carried out and entailing a substantial health risk even when carried out with the required professional care and expertise. The invention does not involve or in particular comprise or encompass any surgical or therapeutic activity. The invention is instead directed as applicable to determining the movement instruction data. The method does not encompass treatment of the patient using radiotherapy and/or radiosurgery. For this reason alone, no surgical or therapeutic activity and in particular no surgical or therapeutic step is necessitated or implied by carrying out the invention.

The present invention also relates to the use of the device/system or any embodiment thereof for correcting the posture of a patient. The use comprises for example at least one of the following steps: the movement instruction data describing movement to be performed is used to move one or more rigid anatomic structures (e.g. comprised in different limbs) of a patient. For example, a display device (e.g. a display screen, an augmented reality device or a light projecting device) is controlled based on the movement instruction display data to output the (movement) instruction. For example, an instruction is output specifying that and/or how a (proximal) rigid anatomic structure (e.g. the upper left arm) of a patient should be moved. The instruction is for example updated from time to time during movement, for example in real-time. Afterwards, an instruction may be output specifying that and/or how a different (e.g. a more distal) rigid anatomic structure (e.g. the lower part of the moved arm/the lower left arm) should be moved. Also in this case, the instruction is for example updated from time to time during movement, for example in real-time. Afterwards, an instruction may be output specifying that and how another rigid anatomic structure of the patient (e.g. the upper right arm) should be moved. The movement of the rigid anatomic structures of the patient may be performed by the patient or by a user or by both. The movement of the patient may be performed until predetermined thresholds of the difference described by the skeleton difference data are met, i.e. until the patient's posture corresponds to a predetermined posture of the patient (posture at the first point in time).

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the World Wide Web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (World Wide Web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Registering

The n-dimensional image of a body is registered when the spatial location of each point of an actual object within a space, for example a body part in an operating theatre, is assigned an image data point of an image (CT, MR, etc.) stored in a navigation system.

Image Registration

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Atlas/Atlas Segmentation

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomic structures in the medical image data which correspond to anatomic structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

Treatment Beam

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts" or "targets". These body parts are for example parts of a patient's body, i.e. anatomical body parts. Ionizing radiation is for example used for the purpose of treatment. For example, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumor are treated using ionizing radiation. The tumor is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Arrangement of Treatment Beams

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

Elastic Fusion, Image Fusion/Morphing, Rigid

The term "matching (image) data" as used in this application relates to image fusion between two sets of (image) data. Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are for example vectors of a deformation field. These vectors are determined by the optimization algorithm in such a way as to result in an optimum degree of similarity. Thus, the optimum degree of similarity represents a condition, for example a constraint, for the optimization algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimizing problem is for example solved iteratively, for example by means of an optimization algorithm which is for example a first-order optimization algorithm, such as a gradient descent algorithm. Other examples of optimization algorithms include optimization algorithms which do not use derivations, such as the downhill simplex algorithm, or algorithms which use higher-order derivatives such as Newton-like algorithms. The optimization algorithm preferably performs a local optimization. If there is a plurality of local optima, global algorithms such as simulated annealing or generic algorithms can be used. In the case of linear optimization problems, the simplex method can for instance be used.

In the steps of the optimization algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

Neutral Bone Position

The neutral position between two bones (an example of a rigid anatomic structure) is a known position in the field of medicine and depends on the type of joint (link). In the hip joint as an example, the neutral position is the position in which the mechanical axis of the femur lies in a sagittal plane, for instance parallel to the midsagittal plane, and the mechanical axis and posterior condylar line of the femur describe a plane which is parallel to the frontal plane of the pelvis. The posterior condylar line connects the most posterior and distal femoral points. It might, however, not be possible to acquire or sample those points, for example during surgery. In this case, an option is to acquire the ankle epicondyle piriformis (AEP) plane defined by a piriformis point (the proximal point of the femur shaft axis), the center of the epicondyle axis and an ankle point of the flexed leg. A direction orthogonal to this AEP plane corresponds to the direction of the posterior condylar axis and thus forms, together with the mechanical axis, a plane which is parallel to the frontal plane of the pelvis in the neutral position.

The neutral position between two bones typically is the origin relative to which a range of motion is defined. This neutral position is achieved for a particular joint orientation of the joint between the two bones. The neutral position can also be defined between two rigid anatomic structures. For example, the neutral position is the origin relative to which a range of motion of the rigid anatomic structures is defined.

Fixed (Relative) Position

A fixed position, which is also referred to as fixed relative position, in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. The spatial location, which is a part of the position, can in particular be described just by a distance (between two objects) or just by the direction of a vector (which links two objects). The alignment, which is another part of the position, can in particular be described by just the relative angle of orientation (between the two objects).

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein

FIG. 7 shows the skeleton model of the patient including a first movement instruction according to the first aspect;

FIG. 8 shows the skeleton model of the patient in a perspective view including the first movement instruction according to the first aspect;

DESCRIPTION OF EMBODIMENTS

Figure 1:
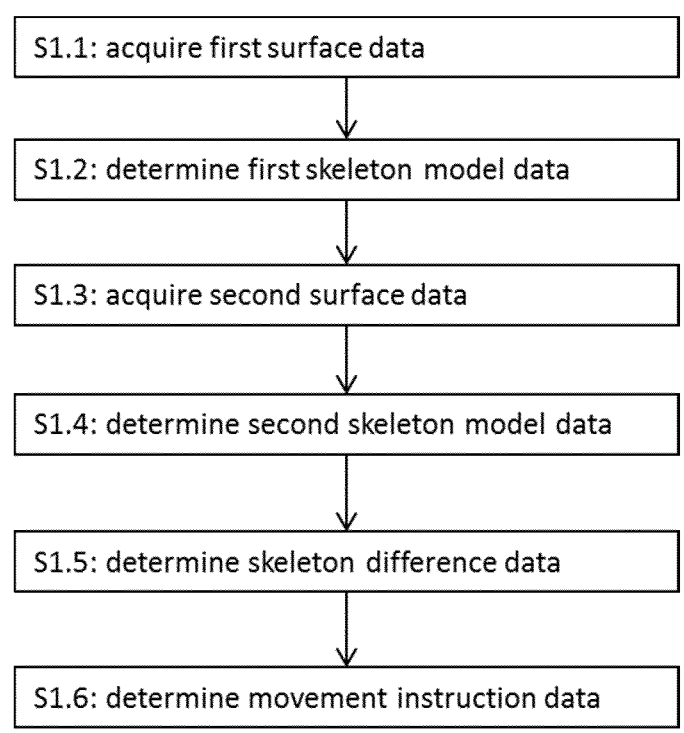
FIG. 1 illustrates the basic steps of the method according to the first aspect.

FIG. 1 illustrates the basic steps of the method according to the first aspect, in which step S1.1 encompasses acquiring the first surface data, step S1.2 encompasses determining the first skeleton model data, step S1.3 encompasses acquiring the second surface data, step S1.4 encompasses determining the second skeleton model data, step S1.5 encompasses determining the skeleton difference data and subsequent step S1.6 encompasses determining the movement instruction data.

Figure 2:
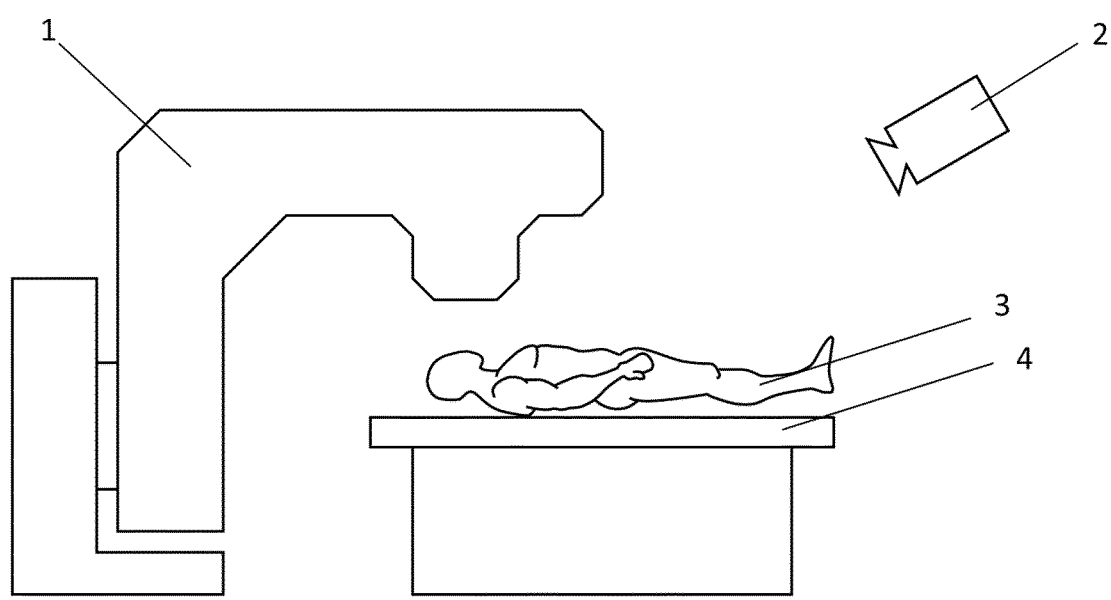
FIG. 2 shows a medical system adapted to perform the method according the first aspect.

FIG. 2 shows a medical system adapted to perform the method according the first aspect. For example, the medical system is a medical system according to the fifth aspect. The medical system comprises a treatment device 1 such as a radiotherapy and/or radiosurgery treatment device, an imaging device 2 (e.g. a 3D scanner, a surface camera, a time-of-flight measurement device, an infrared camera or a stereoscopic camera) and a patient support device 4. The patient 3 is positioned on the patient support device 3. The first, second and third surface data can be acquired with camera 2. The surface of the body of the patient is at least partially in the field of view of camera 2.

Figure 3:
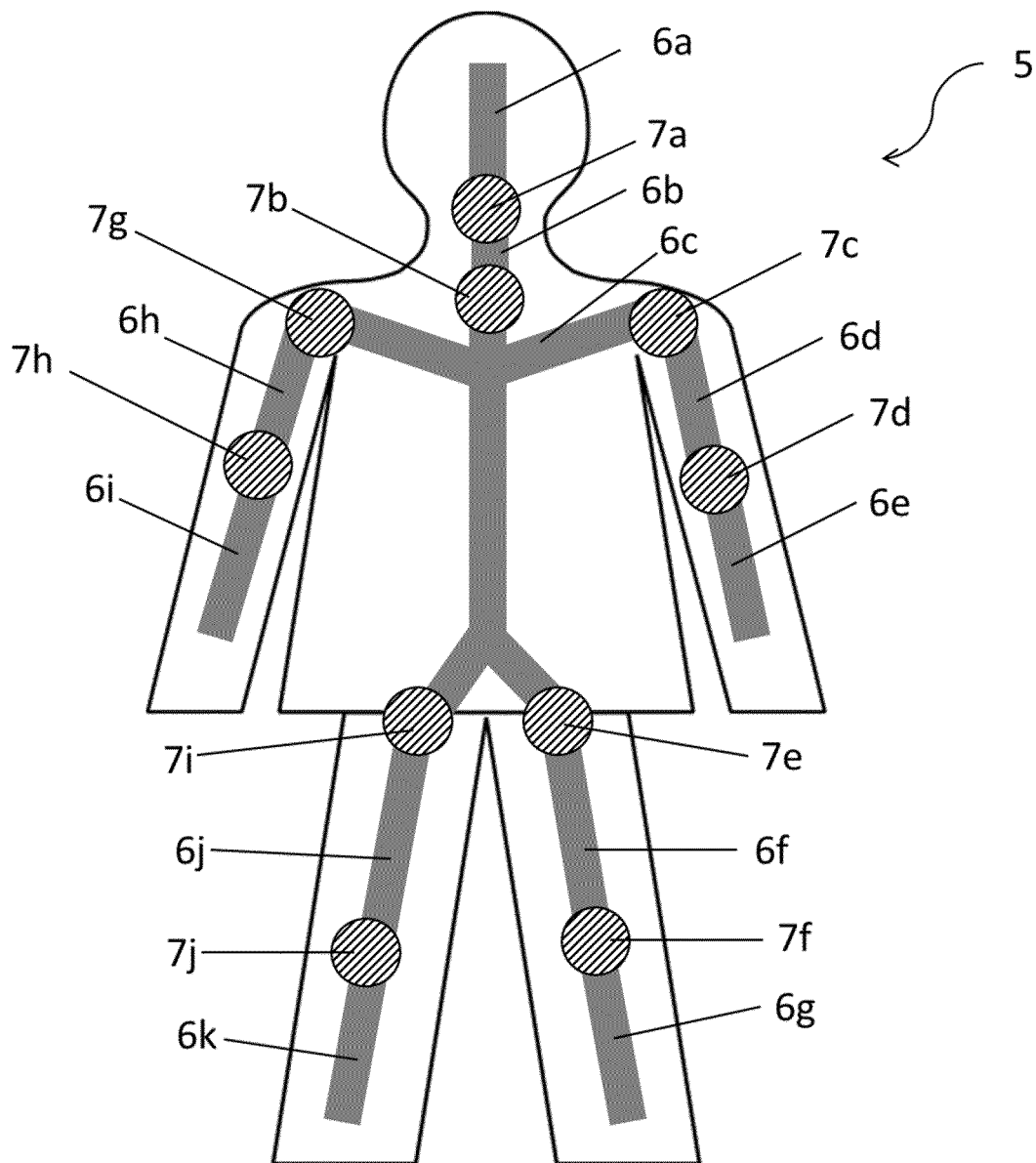
FIG. 3 shows a skeleton model of a patient according to the first aspect.

FIG. 3 shows a skeleton model 5 of a patient according to the first aspect. In particular, FIG. 3 shows first geometries of one or more rigid anatomic structures of the patient as described by the first skeleton model data. In this example, the rigid anatomic structures are indicated with reference signs 6a to 6k. The rigid anatomic structures are joined to each other via links 7a to 7j. Some of the rigid anatomic structures correspond to bones of the patient. For example, 6d represents the upper left arm of the patient, 6i represents the lower right arm of the patient, 6f represents the upper left leg of the patient and 6k represents the lower right leg of the patient. For example, the links 71 to 7j are anatomical joints. For example, 7d represents the left elbow joint of the patient, 7i represents the right hip joint of the patient and 7f represents the left knee joint of the patient. Each of the links 7a to 7j may have a corresponding anatomical movement constraint. For example, the left elbow joint 7d does not enable movement of the lower left arm 6e with respect to the upper left arm 6d into all directions since it is not equivalent to a mechanical ball joint. These anatomical movement constraints can be assigned to each of the links 7a to 7j and/or to each of the rigid anatomic structures 6a to 6k and may be patient-specific.

Figure 4:
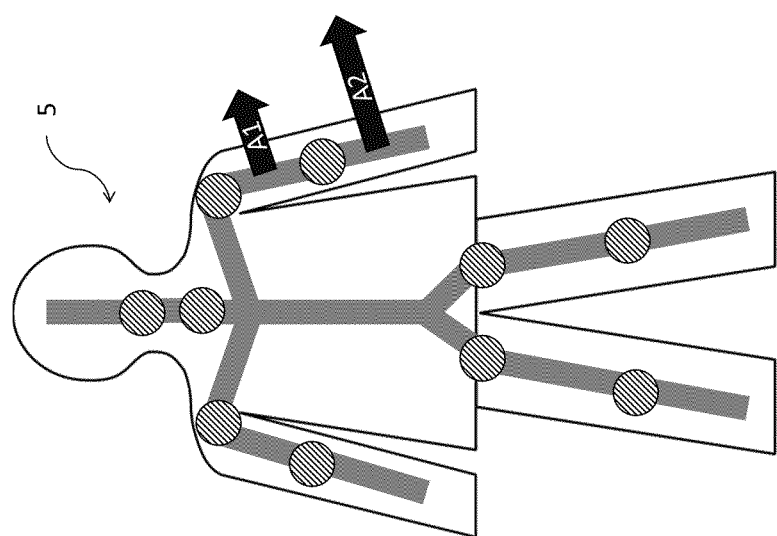
FIG. 4 shows the skeleton model of the patient including two movement instructions according to the first aspect.

FIG. 4 shows the skeleton model of the patient including two movement instructions according to the first aspect. In particular, FIG. 4 shows the first geometries of the one or more rigid anatomic structures 6a to 6k of the patient as described by the first skeleton model data and as explained above with respect to FIG. 3. Additionally, FIG. 4 shows two movement instructions. In particular, an instruction specifying movement to be performed by the upper left arm 6d of the patient and an instruction specifying movement to be performed by the lower left arm 6e of the patient are shown. In this example, the instructions specifying movement to be performed are displayed as arrows A1 and A2. These arrows are for example displayed by a display device based on the movement instruction display data describing an instruction specifying movement to be performed. Additionally, the skeleton model 5 can be displayed.

Figure 5:
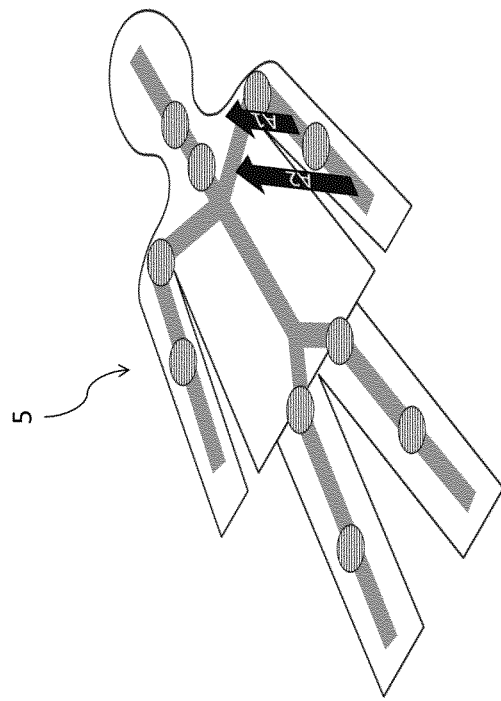
FIG. 5 shows the skeleton model of the patient in a perspective view including the two movement instructions according to the first aspect.

FIG. 5 shows the skeleton model 5 of the patient in a perspective view including the two movement instructions according to the first aspect. For example, the display device is an augmented reality device which displays the skeleton model 5 and/or the arrows A1 and A2 in a perspective similar to that as the user sees the patient. In this example, the user stands at the side of the left foot of the patient and looks down onto the patient.

Figure 6:
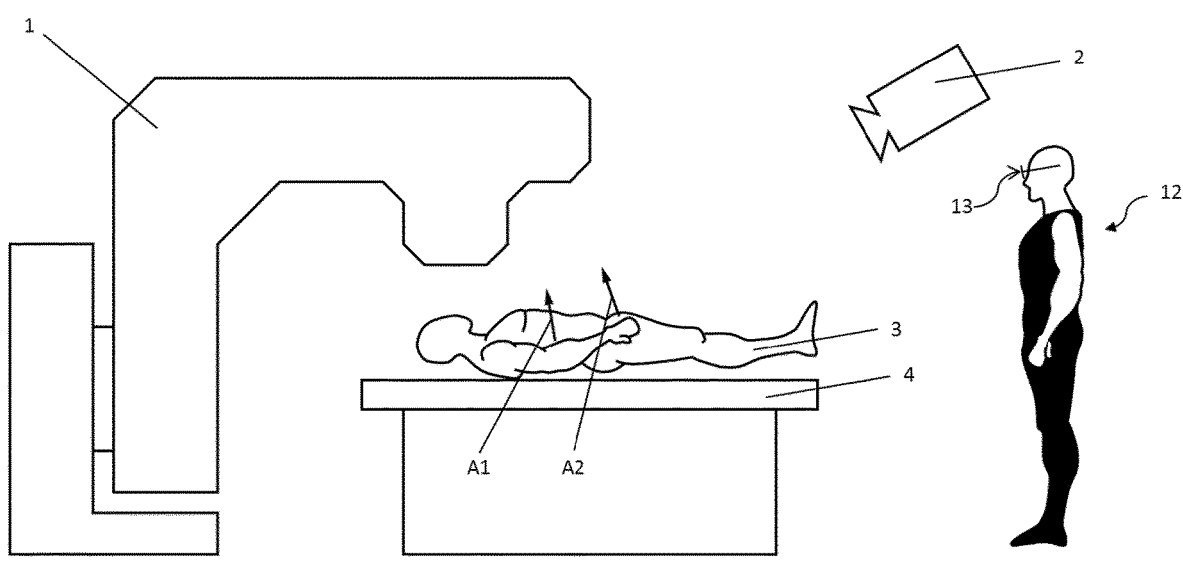
FIG. 6 shows a medical system adapted to perform the method according the first aspect and a user of the medical system.

FIG. 6 shows a medical system adapted to perform the method according the first aspect and a user 12 of the medical system. The arrangement shown is mostly similar to the one described above with respect to FIG. 2, therefore description of the corresponding parts (e.g. 1, 2, 3 and 4) is omitted at this point. FIG. 6 shows a user 12 of the medical system. In this example, an augmented reality device 13 is used as the display device (e.g. augmented reality glasses). The arrows A1 and A2 correspond to the arrows A1 and A2 described above with respect to FIG. 4 and FIG. 5 and are displayed on the augmented reality device 13 to the user 12. Of course, other means of displaying the instructions specifying movement to be performed—different from the arrows A1 and A2—are possible as described earlier.

FIG. 7 shows the skeleton model 5 of the patient including a first movement instruction according to the first aspect. In this case, only arrow A1 is displayed as specifying movement to be performed by the more proximal part of the limb of the patient (here movement to be performed by the upper left arm 6d).

FIG. 8 shows the skeleton model 5 of the patient in a perspective view including the first movement instruction according to the first aspect. Also in this case, the display device may be an augmented reality device which displays a perspective view of the patient and/or of the movement instruction, e.g. the arrow A1.

Figure 9:
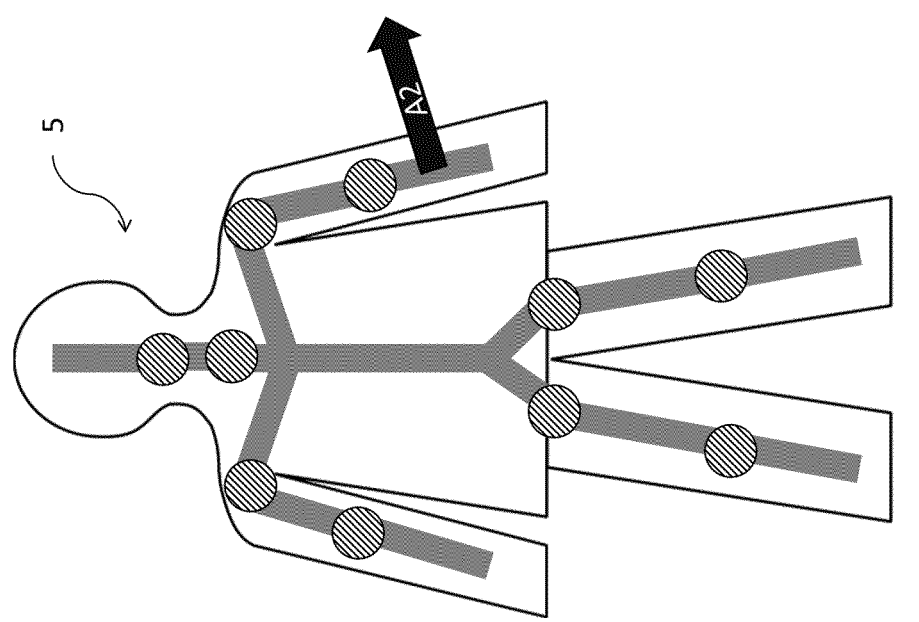
FIG. 9 shows the skeleton model of the patient including a second movement instruction according to the first aspect.

FIG. 9 shows the skeleton model of the patient including a second movement instruction according to the first aspect. For example, the upper arm of the patient was moved in accordance with the instruction shown in FIGS. 7 and 8. The method according to the first aspect may then determine that the posture of the patient was changed and update the movement instruction data correspondingly based on the third surface data (i.e. the current surface of the body of the patient). The instruction in this example specifies movement to be performed by a more distal rigid anatomic structure (i.e. the lower left arm 6e). An arrow A2 is used for that purpose. As in the previous case, the arrow may be displayed on the display device together with the skeleton model 5 or individually or may be projected onto the patient. Of course, other means to indicate the movement instruction are possible: color-coding, numbers, arrows, symbols, text, vectors, curved arrows, animations, the desired pose or combinations thereof.

Figure 10:
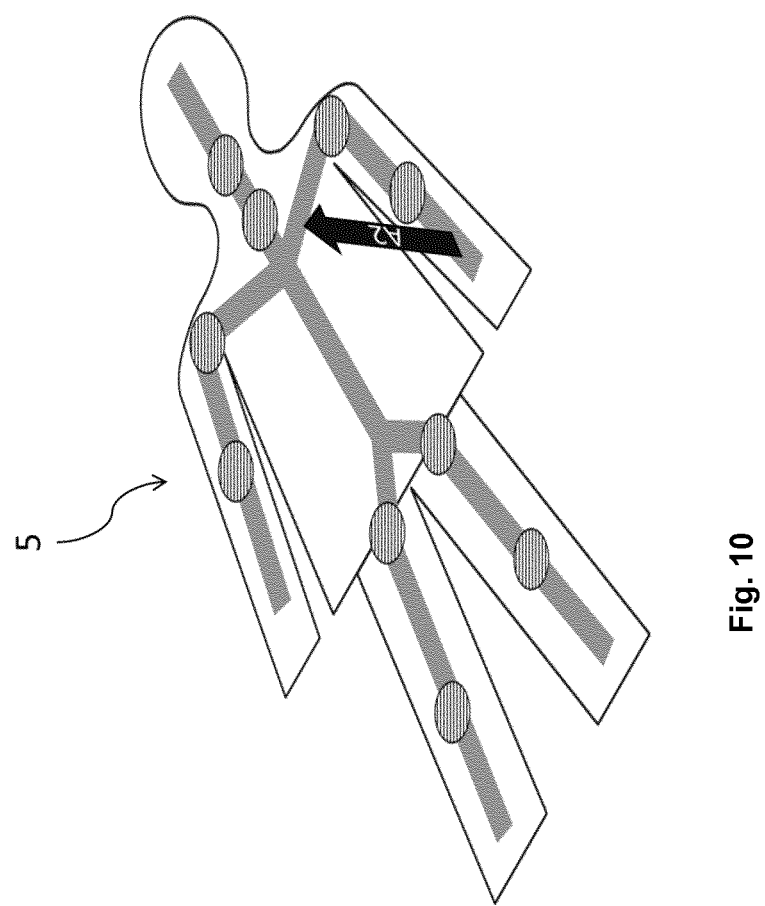
FIG. 10 shows the skeleton model of the patient in a perspective view including the second movement instruction according to the first aspect.

FIG. 10 shows the skeleton model of the patient in a perspective view including the second movement instruction according to the first aspect. Also in this case, the display device may display the skeleton model 5 together with the arrow A2 or only display arrow A2 in a perspective view, e.g. in a point-of-view of a user of the medical system.

Figure 11:
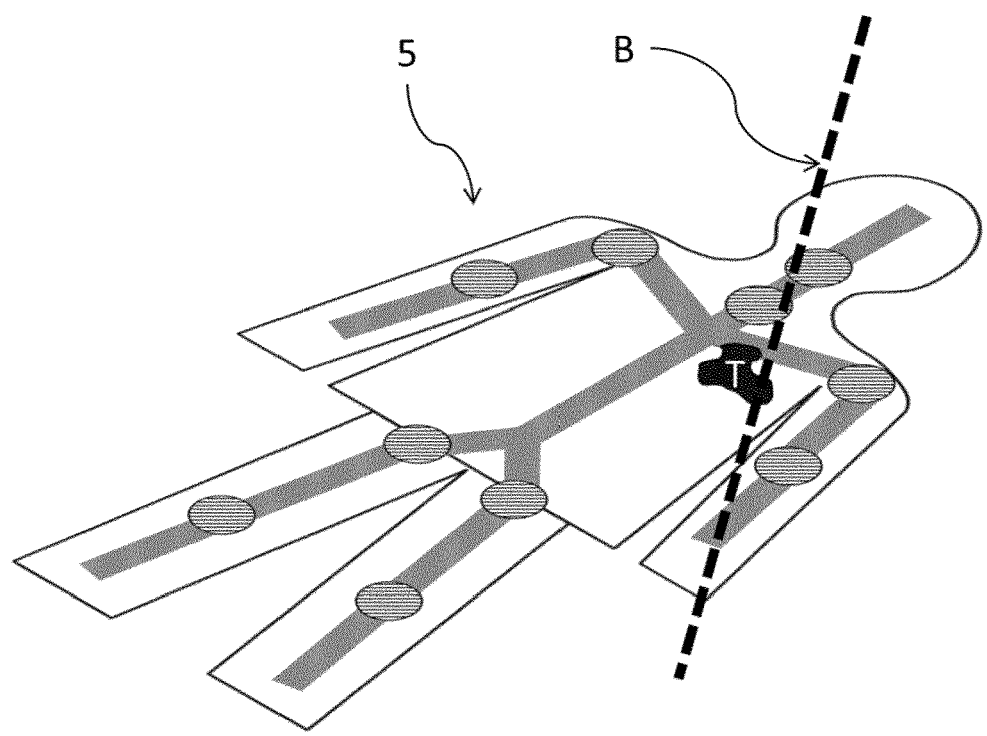
FIG. 11 shows the skeleton model of the patient in a perspective view including a target and a simulated treatment beam according to the first aspect.

FIG. 11 shows the skeleton model 5 of the patient in a perspective view including a target T and a simulated treatment beam B according to the first aspect. In this case, target data was acquired and corrected target data was determined based on the surface deviation data and based on the target data. This means that the current position of the target is shown based on the current posture of the patient. For example, a virtual object corresponding to the geometry of the target is output by the display device (T in FIG. 11). Also, the position and shape and/or the arrangement of one or more treatment beams (beam arrangement) can be simulated and displayed as well. This is indicated by simulated treatment beam B which runs through the virtual object T representing the target (e.g. tumor).

Figure 12:
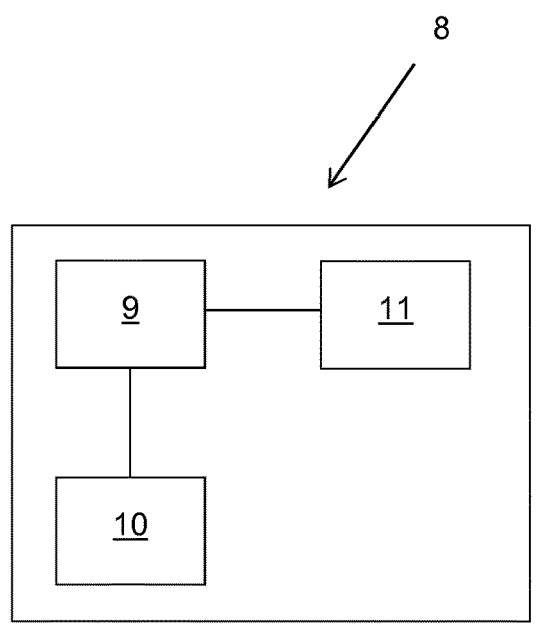
FIG. 12 is a schematic illustration of the system according to the fifth aspect.

FIG. 12 is a schematic illustration of the medical system 8 according to the fifth aspect. The system is in its entirety identified by reference sign 8 and comprises a computer 9, an electronic data storage device (such as a hard disc) 10 for storing at least the first surface data and a medical device 11 (such as a radiation treatment apparatus). The components of the medical system 8 have the functionalities and properties explained above with regard to the fifth aspect of this disclosure.

The invention also relates to an embodiment as described below:

The general setup is shown in FIG. 2. A surface representation of a patient 3 positioned on a patient positioning device 4 is generated. Said representation is generated using information provided by an imaging device 2 (e.g. a 3D-scanner using structured-light, modulated-light or time-of-flight). The patient's surface is captured by an imaging device 2, i.e. the 3D-scanner. This surface representation (e.g. the second surface data) is used to compare it against the surface of a (3-D) representation of the patient (e.g. first surface data), which is stored in memory. Said representation was acquired by using a (3-D) scanner or a (medical) imaging device. Said comparison is calculated using algorithms like Iterative Closest Point (see e.g. P. J. Besl et al., "A Method for Registration of 3-D Shapes", IEEE Transactions on Pattern Analysis and Machine Intelligence 14(2), 1992, pp. 239-256) or Normal Distribution Transform (see e.g. P. Biber et al., "The Normal Distributions Transform: A New Approach to Laser Scan Matching", IEEE International Conference on Intelligent Robots and Systems, 2003, vol. 3, pp. 2743-2748).

Also, an anatomically correct mechanical representation of the patient's body is created in the form of a so-called skeleton model (e.g. skeleton model 5) by using a model considering the degrees of freedom of every individual joint (e.g. links 7a to 7j) and the (3-D) representation as shown in FIG. 3. Said mechanical representation can be simplified using multiple levels of simplification. Said mechanical representation is created by using algorithms as described in J. Shotton, et al.: "Real-time human pose recognition in parts from single depth images", IEEE Conference on Computer Vision and Pattern Recognition (CVPR), 2011, pp. 1297-1304.

Afterwards, the comparison of the detected (e.g. second surface data) and the stored (e.g. first surface data) surface representation is used to calculate the deviation, i.e. translation and rotation, for each body part with respect to the mechanical model (e.g. skeleton difference data) and display that information to the user (e.g. movement instruction (display) data) using a display device (e.g. augmented reality device). The information can be shown to the user as vectors (straight arrows), curved arrows, animations, color-coding or as the desired pose.

Also, the relative position of a target (e.g. the tumor to be irradiated) to the for example three-dimensional (3-D) representation of the patient's body is loaded. Then, the current position of the target is calculated based on the detected surface representation (e.g. the second surface data) and that information is displayed (e.g. target display data) to the user via a display device (e.g. an augmented reality device) as shown in FIG. 11.

Also, planned beams can be loaded from a radiation plan. Information about the current position of the gantry can be obtained from the gantry control system of the radiation treatment device. Representations of the beams B can then be displayed to the user (who is for example using an augmented reality device) as shown in FIG. 11. It can also be displayed how well the target would be hit in the scenario as defined by the current position of the gantry and the position and/or posture of the patient.

With the calculated deviation for each rigid anatomic structure the user can be guided in a very precise way so that the actual posture of the patient matches the desired one precisely. This is done by virtually showing (e.g. displaying) vectors and/or paths, color-coding, and/or the desired pose, so that the user knows exactly how the patient's desired posture looks like and how to get the patient into this posture.

The displaying of the target using augmented reality (e.g. as described with respect to FIG. 6) especially in combination with a virtual representation of the radiation beams gives the user an even better feedback of how correct the patient current position and/or posture are.

The invention claimed is:

1. A computer-implemented medical method for determining a movement instruction for correcting posture of a patient having a body part, the method comprising:
    acquiring first three-dimensional surface data that describes an outer three-dimensional contour of the body part of the patient imaged at a first point in time to generate the first three-dimensional surface data;
    determining first skeleton model data based on the first three-dimensional surface data, wherein the first skeleton model data describes first geometries of one or more rigid anatomic structures of the patient;
    acquiring second three-dimensional surface data that describes the outer three-dimensional contour of the body part of the patient imaged at a second point in time to generate the second three-dimensional surface data;
    determining second skeleton model data based on the second three-dimensional surface data, wherein the second skeleton model data describes second geometries of the one or more rigid anatomic structures of the patient;
    determining skeleton difference data based on the first skeleton model data and on the second skeleton model data, wherein the skeleton difference data describes a difference between the first geometries and the second geometries; and
    determining movement instruction data based on the skeleton difference data and the second skeleton model data, wherein the movement instruction data describes movement to be performed by the one or more rigid anatomic structures in order to minimize the difference between the first and second geometries.

2. The method according to claim 1, further comprising:
    acquiring anatomy constraint data that describes anatomical movement constraints for the one or more rigid anatomic structures, wherein the anatomical movement constraints comprise range of motion constraints,
    wherein the determining the movement instruction data comprises determining the movement instruction data based on the anatomy constraint data.

3. The method according to claim 2, wherein the anatomy constraint data describes the anatomical movement constraints for at least one of the one or more rigid anatomic structures specifically for the patient.

4. The method according to claim 1, further comprising determining the movement instruction data starting with the determination of the movement to be performed by those of the one or more rigid anatomic structures which are comprised in the same limb of the patient.

5. The method according to claim 1, wherein the movement instruction data is determined starting with the determination of the movement to be performed by the most proximal of the rigid anatomic structures and/or ending with the determination of the movement to be performed by the most distal of the rigid anatomic structures.

6. The method according to claim 1, further comprising:
    determining surface deviation data based on the first three-dimensional surface data and the second three-dimensional surface data, wherein the surface deviation data describes deviations between the outer three-dimensional contour of the body part of the patient at the first point in time and the outer three-dimensional contour of the body part of the patient at the second point in time.

7. The method according to claim 6, further comprising:
    acquiring target data that describes a geometry of a target for treatment at the first point in time; and
    determining corrected target data based on the surface deviation data and based on the target data, wherein the corrected target data describes the geometry of the target at the second point in time.

8. The method according to claim 7, further comprising:
    determining target display data based on the corrected target data, wherein the target display data describes a virtual object corresponding to the geometry of the target at the second point in time; and
    controlling a display device based on the target display data to output the virtual object.

9. The method according to claim 1, further comprising:
    determining movement instruction display data based on the movement instruction data, wherein the movement instruction display data describes an instruction specifying movement to be performed by at least one rigid anatomic structure; and
    controlling a display device based on the movement instruction display data to output the instruction.

10. The method according to claim 9, wherein the instruction specifies movement to be performed by those of the one or more rigid anatomic structures which are comprised in the same limb of the patient.

11. The method according to claim 1, further comprising after acquiring the second three-dimensional surface data:
    acquiring third three-dimensional surface data describing the outer three-dimensional contour of the body part of the patient at a third point in time;
    determining decision data based on the second three-dimensional surface data and the third three-dimensional surface data, wherein the decision data specifies whether a rigid anatomic structure of the patient has changed between the second point in time and the third point in time; and
    repeating the method starting with the acquiring the second three-dimensional surface data, if the decision data specifies that the posture of the patient has changed between the second point in time and the third point in time,
    wherein, while repeating the method, the third point in time is used as the second point in time.

12. The method according to claim 11, wherein at least one of the first three-dimensional surface data, the second three-dimensional surface data or the third three-dimensional surface data is or has been obtained from a series of two-dimensional images of the body part of the patient.

13. The method according to claim 11, wherein at least one of the first three-dimensional surface data, the second three-dimensional surface data or the third three-dimensional surface data is or has been obtained from one or more of a cone-beam (CB) computer-tomographic (CT) image, a magnetic resonance (MR) image, a depth-image, a parallax image, and/or an anatomical atlas describing the body part of the patient.

14. A program logic stored in a memory device of a computer, that when running on the computer or when loaded onto the computer, causes the computer to perform a method comprising:
    acquiring first three-dimensional surface data that describes an outer three-dimensional contour of a body part of a patient imaged at a first point in time to generate the first three-dimensional surface data;

determining first skeleton model data based on the first three-dimensional surface data, wherein the first skeleton model data describes first geometries of one or more rigid anatomic structures of the patient;

acquiring second three-dimensional surface data that describes the outer three-dimensional contour of the body part of the patient imaged at a second point in time to generate the second three-dimensional surface data;

determining second skeleton model data based on the second three-dimensional surface data, wherein the second skeleton model data describes second geometries of the one or more rigid anatomic structures of the patient;

determining skeleton difference data based on the first skeleton model data and on the second skeleton model data, wherein the skeleton difference data describes a difference between the first geometries and the second geometries; and determining movement instruction data based on the skeleton difference data and the second skeleton model data, wherein the movement instruction data describes movement to be performed by the one or more rigid anatomic structures in order to minimize the difference between the first geometries and the second geometries.

15. A medical system, comprising:

at least one computer;

at least one electronic data storage device storing at least first three-dimensional surface data that describes an outer three-dimensional contour of a body part of a patient imaged at a first point in time to generate the at least first three-dimensional surface data; and a medical device for carrying out a medical procedure on the patient, the medical device comprising a display device, wherein the at least one computer is operably coupled with:

the at least one electronic data storage device for acquiring, from the at least one data storage device, at least the first three-dimensional surface data, and the medical device for issuing a control signal to the medical device for controlling, on the basis of movement instruction data, displaying, by the display device, an instruction specifying movement to be performed by one or more rigid anatomic structures of the patient.

16. The medical system according to claim 15, wherein:

the at least one computer is operable to:

acquire the first three-dimensional surface data that describes the three-dimensional outer contour of the body part of the patient imaged at a first point in time to generate the first three-dimensional surface data;

determine first skeleton model data based on the first surface data, wherein the first skeleton model data describes first geometries of one or more rigid anatomic structures of the patient;

acquire second three-dimensional surface data that describes the outer three-dimensional contour of the body part of the patient imaged at a second point in time to generate the second three-dimensional surface data;

determine second skeleton model data based on the second surface data, wherein the second skeleton model data describes second geometries of the one or more rigid anatomic structures of the patient;

determine skeleton difference data based on the first skeleton model data and on the second skeleton model data, wherein the skeleton difference data describes a difference between the first geometries and the second geometries; and determine the movement instruction data based on the skeleton difference data and the second skeleton model data, wherein the movement instruction data describes the movement to be performed by the one or more rigid anatomic structures in order to minimize the difference between the first and second geometries.

\* \* \* \* \*